United States Patent [19]

Brodard

[11] Patent Number: 5,033,469

[45] Date of Patent: Jul. 23, 1991

[54] INSTALLATION FOR NEUROMUSCULAR ELECTRICAL STIMULATION

[75] Inventor: Roland Brodard, Villeneuve, Switzerland

[73] Assignee: Medicompex S.A., Geneva, Switzerland

[21] Appl. No.: 522,475

[22] Filed: May 11, 1990

Related U.S. Application Data

[63] Continuation of Ser. No. 268,805, Nov. 8, 1988, abandoned.

[30] Foreign Application Priority Data

Nov. 12, 1987 [CH] Switzerland .......................... 4416/87

[51] Int. Cl.$^5$ ............................................. A61N 1/08
[52] U.S. Cl. .................................................. 128/421
[58] Field of Search .................... 128/421, 422, 423 R

[56] References Cited

FOREIGN PATENT DOCUMENTS 1175493 10/1984 Canada ................................. 128/421
0087617 9/1983 Fed. Rep. of Germany ...... 128/421
0197889 10/1986 Switzerland .......................... 128/421

*Primary Examiner*—William E. Kamm
*Assistant Examiner*—Scott M. Getzow
*Attorney, Agent, or Firm*—Trexler, Bushnell, Giangiorgi & Blackstone, Ltd.

[57] ABSTRACT

The programming device (1) and the stimulating device (2) are capable of independent operation. An on-line link (3) enables them to be connected when they interact. The programming device (1) is used for editing memory cards (12) of the smart card type, designed to record complete treatment programs individualized per patient, when these cards are placed in a receiver (11) equipped with a connector (38) designed to interact with a connector (37) of this card (12). The stimulating device (2) is arranged to operate independently under the control of such a memory card placed in its receiver (25). The on-line link makes it possible, in particular, to modify by means of the keyboard (8) the program recorded on a memory card (12) and in the memory (7) of the programming device (1), in accordance with the reactions of the patient subjected to this program by means of the stimulating device (2), in order to individualize and adapt the program to each patient.

When the stimulating device (2) is operating independently, the latter records times of use by the patient on the memory card (12) which controls the device, for purposes of monitoring observance.

6 Claims, 6 Drawing Sheets

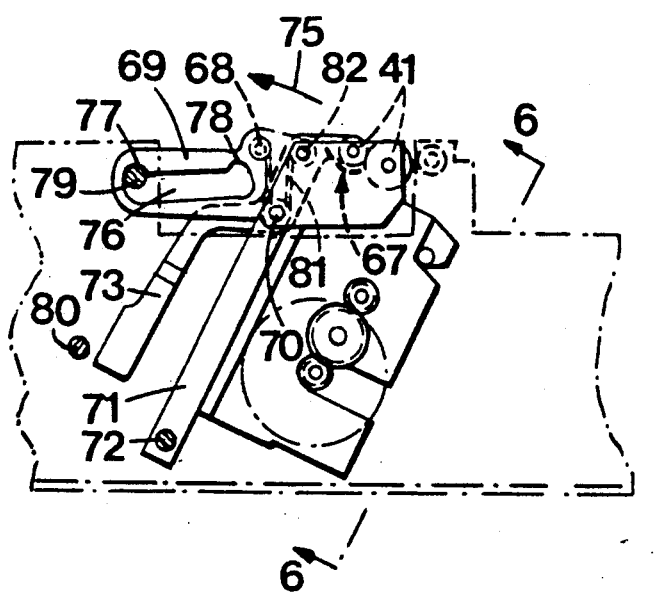
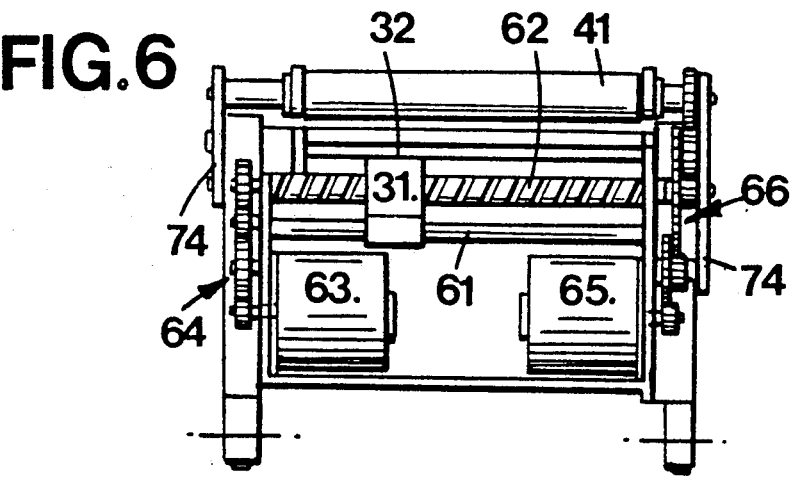
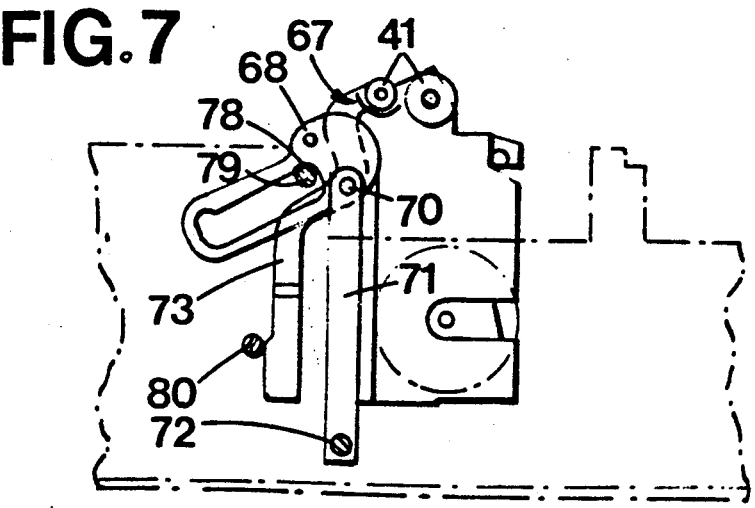

5,033,469

INSTALLATION FOR NEUROMUSCULAR ELECTRICAL STIMULATION

This application is a continuation of application Ser. No. 268,805, filed Nov. 8, 1988, now abandoned.

BACKGROUND OF THE INVENTION

Installations comprising a programming device and a stimulating device operating independently of one another are already known. The programming device is constructed so as to record a treatment program on a fixed-storage data medium, and this data medium carrying the program is placed in the stimulating device in order to control it and to have the program executed.

The drawback of this system is its inflexibility, that is to say, the program thus recorded is immediately permanent, and cannot be adapted in a precise manner to the patient's case as a result of the use of ROMs.

Moreover, an installation comprising a programming device and a stimulating device capable of on-line working is known. However, in this case, there is no data medium independent of the two devices, the programming device having the role of enabling a program established by the therapist to be recorded in an RAM of the stimulating apparatus. The drawback is that, every time the stimulating device has to be used by a different patient, the program which it has received previously has to be erased and the program relating to the new patient has to be recorded again. Once the first program has been erased, no trace of it has been left anywhere and, when the first patient has to be treated again, it is necessary to re-record the program appropriate to him in the stimulating device once again. This results in excessive delays in the treatments and an irrational use of the hardware, with the possibility of risk of errors due to successive re-introductions of the same program at longer or shorter time intervals.

The present invention aims to provide an installation for neuromuscular electrical stimulation which is free from all the defects which have just been noted and which accordingly enables, on the one hand, a completely individualized program to be established for each patient, taking into account the physiological and pathological features of the patient. In addition, the installation has to ensure the patient's safety by subjecting the treatment to imposed limits in the intensity and duration of the currents used. This installation must, in addition, enable the same stimulating device to be used successively for different patients, without loss of time, that is to say by having this stimulating device controlled by different data media each corresponding to a particular patient, each of these data media containing a patient's individualized program. Thus, on the one hand each individualized program remains continuously available on the data medium and does not have to be retyped by the therapist; and on the other hand, the stimulating device is immediately available when there is a change of patient, since it then suffices to introduce into this device the data medium corresponding to the patient.

THE INVENTION

The installation for neuromuscular stimulation according to the invention is as claimed in claim 1.

BRIEF DESCRIPTION OF THE DRAWINGS

The attached drawing shows diagrammatically and by way of example an embodiment of the installation according to the invention.

FIG. 5 is a detail view corresponding to FIG. 4 and showing the printing mechanism in the working position.

FIG. 6 is a side view according to the arrow 6 of FIG. 5.

FIG. 7 is a view similar to FIG. 5, but showing the printing mechanism in the position of introduction of the paper.

PREFERRED EMBODIMENTS OF THE INVENTION

Figure 1:
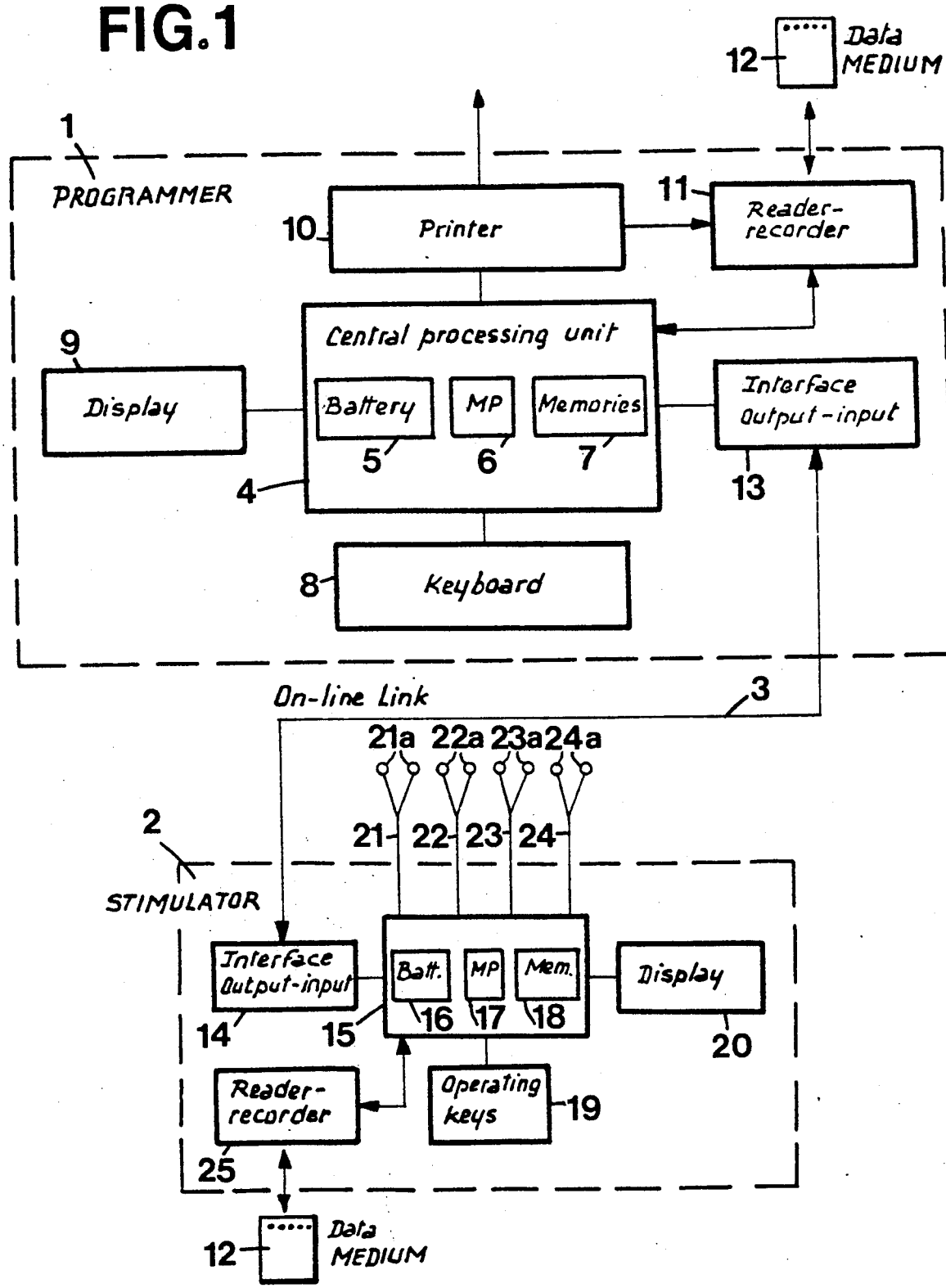
FIG. 1 is a block diagram of the whole installation.

The installation shown in the block diagram of FIG. 1 comprises a programming device 1, a stimulating device 2 and an on-line link 3 enabling these two devices to be made to work together, as will be seen below.

The programming device comprises a central processing unit 4 which contains a current source 5, a microprocessor 6 and memories 7, including the program memories. A keyboard 8 enables the operator to act on the central processing unit 4. This device also comprises a display facility 9, enabling the operator, in particular, to check his work on the keyboard. This device comprises, in addition, a unit 10 for printing on self-adhesive paper tape, a receiving facility 11 equipped with a connector and designed to receive temporarily a data medium 12, also equipped with a connector. This receiving facility enables data to be transmitted from the central processing unit 4 to the data medium 12, and vice versa. The programming device finally comprises an interface 13, used for the output and input of data via the on-line link 3.

The stimulating device comprises an interface 14 permitting the exchange of data with the programming device via the on-line link 3. This interface 14 is connected to the central processing unit 15, comprising a current source 16, a microprocessor 17 and memories 18. A set of control keys 19 is provided for controlling the operations of this stimulating device. A display 20 is linked to the central processing unit 15.

Four outputs 21, 22, 23, 24 connect the central processing unit to pairs of electrodes 21a, 22a, 23a, 24a, designed to be applied at different points on the patient's body. The stimulating device finally comprises a receiving facility 25 equipped with a connector and designed to receive the data medium 12 already mentioned in connection with the programming device. This receiving facility is arranged to interact in both directions with the central processing unit 15. The operation of the installation shown diagrammatically in FIG. 1 is as follows.

The first step is to record on the data medium 12 a program of individualized electrical stimulation, that is to say a program fully matched to the physiology and pathology of a particular patient. At this point, the on-line link 3 is not needed. The therapist has at his disposal a collection of data media such as 12, on which different standard stimulation programs are recorded and which constitute a kind of program library. The operator, now dealing with a particular patient, arranges a data medium, equipped with the standard program which may best correspond to the patient, in the receiving facility 11, and he then orders the transfer of this standard program into a program memory of the block 7. When this has been done, he replaces the data medium containing the standard program in the receiving facility 11 by a blank data medium. The therapist then has to adapt this standard program to the patient's particular case, more fully than could be done by the standard program. To this end, he uses the keyboard 8 to introduce the modifications and additions to the standard program. These modifications and additions are transferred to the program memory contained in the unit 7. When this has been done, he transfers the standard program, thus modified, from the memory 7, via the microprocessor 6, to the blank data medium 12 placed in the receiving facility 11.

When this has been done, the therapist has the possibility of further improving the program recorded on the medium 12, by adapting it more to the patient's particular conditions as regards the latter's reaction during the treatment. The on-line link 3 is then established and the patient's data medium 12 is placed in the receiving facility 25 of the stimulating device. The electrodes 21a, 22a, 23a, 24a are applied to the selected points on the patient and the latter is subjected to stimulation under the control of the program, modified a first time, recorded on the medium 12. The therapist observes the patient's behavior and reactions during the different stages of execution of the program, and adapts the program exactly to the patient by proceeding as follows. In the first place, by observing the patient during the test, he uses the keyboard 8 to record, via the microprocessor 6, the maximum and minimum limits of current intensity permissible for this patient, for each of the outputs 21, 22, 23 and 24. When this has been done, the therapist still has the possibility of refining the program by modifying it in certain respects according to the patient's reactions, which he will have observed during the test. The fixing of the output current maxima and minima is necessary for the patient's safety, and also in the interest of the efficacy of the treatment. All these data, that is to say permissible maxima and minima and modifications of the program, are recorded simultaneously on the medium 12 and in the memories 7 and 18. From this point, the patient's treatment can begin. The on-line link can then be removed and, from then on, the medium 12 controls the stimulating device 2. The program runs under the operator's control by means of the keys of the operating keyboard 19.

In the foregoing description, it is seen that the program applied to the patient is established in three stages: the procedure begins with the pre-existing standard program, which is adapted to a certain extent to the patient's case using the keyboard 8, and then, in a third stage, the program is completed or modified once again by using the keyboard 8 on the basis of the patient's observed reactions during the test. In fact, the second stage is not essential, and it is perfectly possible to proceed in two stages, the first being the recording of a standard program and, in the second phase, with the on-line link, the current maxima and minima permissible at the outputs are recorded and the adaptation of the standard program to the patient's particular case is made using the keyboard 8. Aa regards the library of standard programs, this is formed by arranging a blank card in the receiving facility 11 in every case and a standard program is typed in on the keyboard 8. Once this program has been recorded on the data medium, the latter may be removed and constitutes one of the standard programs. It is also possible to make a standard program supplemented or modified according to experiments carried out subsequently, in order to be able to have at one's disposal an additional standard card that is better matched. The procedure will be as follows: the data medium containing the standard program is placed in the receiving facility 11. The transfer of this program into one of the memories 7 is ordered through the keyboard 8, and the keyboard 8 is then used to introduce the desired modifications and additions to the standard program, which are then recorded in one of the memories 7. Then, under the control of the keyboard, this modified program is transferred onto a blank data medium which has been placed in the receiving facility 11 as a replacement for the standard program. From that point, a new modified standard program is at one's disposal in the library.

The data media such as 12 are preferably of the smart card type, and can advantageously assume the format of an ordinary credit card.

The installation described offers, in addition to what has been stated, the advantage of enabling the therapist to monitor the patient's observance of the program of stimulation which he has to undergo using the stimulating device 2. It has been seen above that the maximum and minimum values of the current permissible for the patient in question in each of the outputs 21, 22, 23 and 24 are recorded on the patient's data medium 12. During the establishment of the personalized program, the therapist records on the individualized data medium 12, by actuating the keyboard 8, the period laid down for the treatment according to this program.

Under these conditions, to check the observance on the patient's part, the therapist has only to place the patient's data medium 12 in the receiving facility 11 of the device and, through the keyboard 8 and via the microprocessor 6, he interrogates the data medium 12 which, through the display at 9 and, where appropriate, by printing on a paper tape at 10, provides the actual during which the stimulating device has operated during the previous treatment and the period during which, for each of the outputs 21, 22, 23, 24, the intensity of the working current in these outputs was within the minimum and maximum limits programmed and recorded on the medium 12. The therapist hence receives the reply to his question in the form of a time period. If some periods are missing, it means that the patient has not complied with the treatment laid down, and the therapist can intervene.

Figure 2:
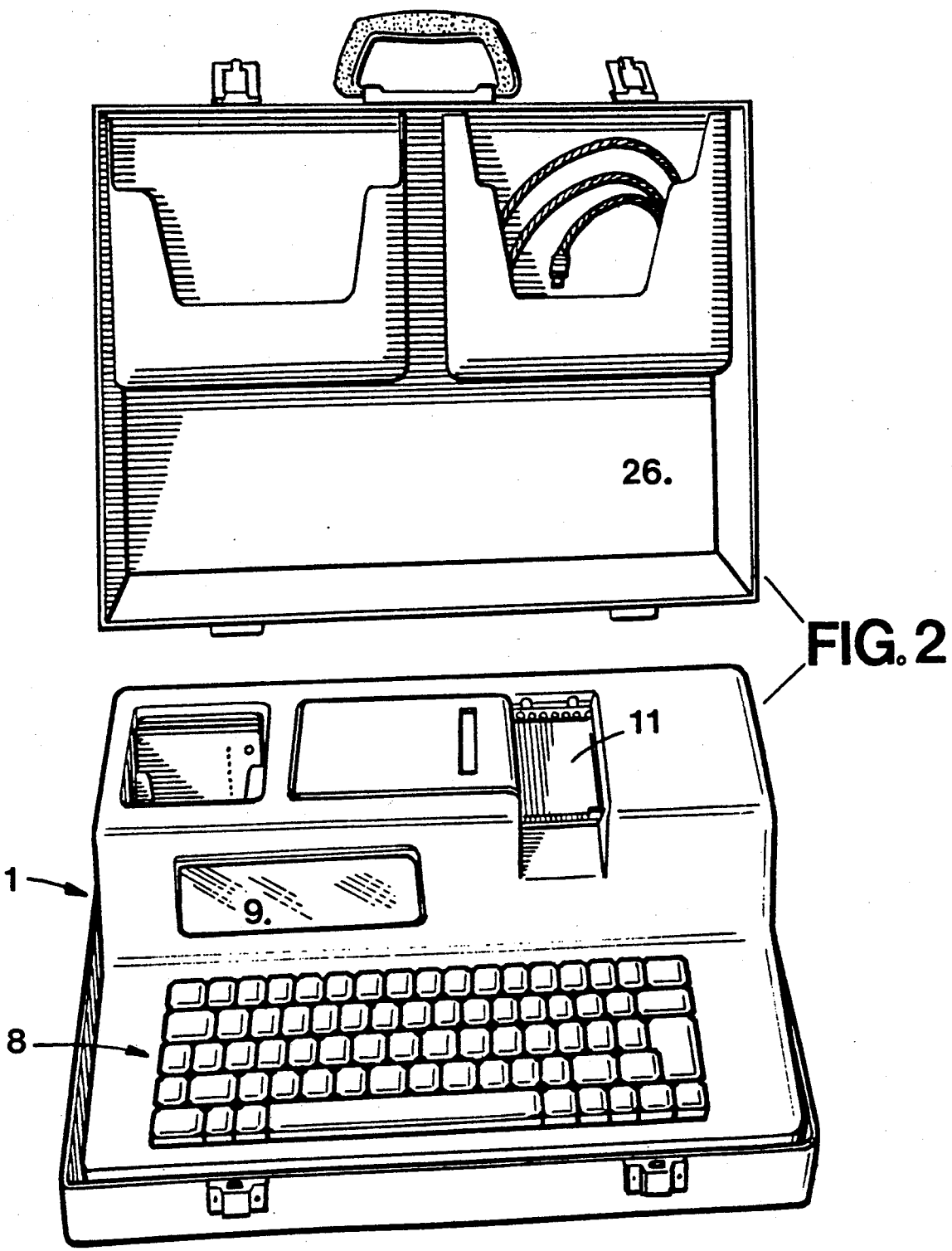
FIG. 2 shows the programming device with its removable lid in the open position.
Figure 3:
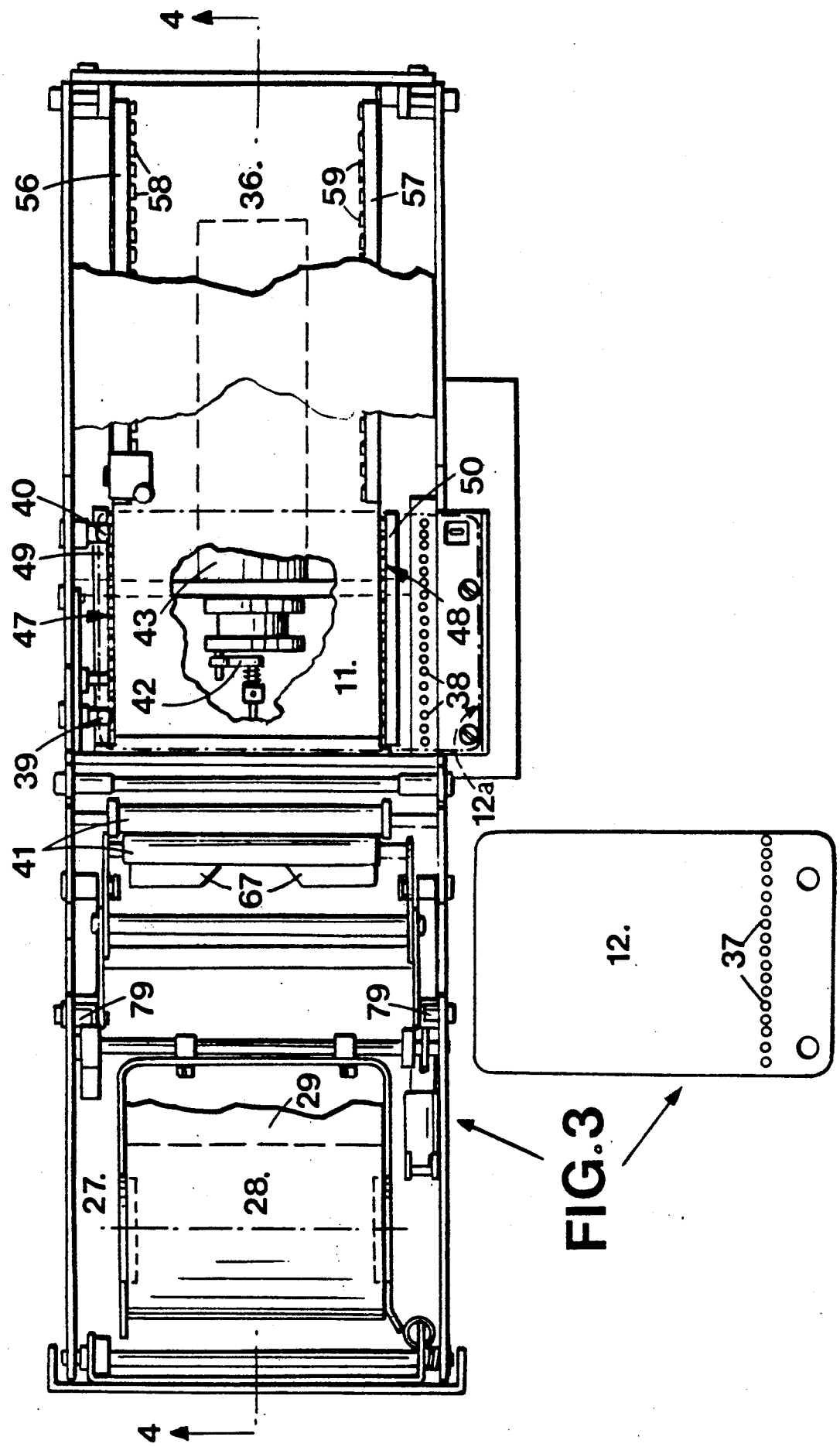
FIG. 3 is a plan view of the mechanical part of the programming device, which is concealed in FIG. 2 by the casing of this device.
Figure 4:
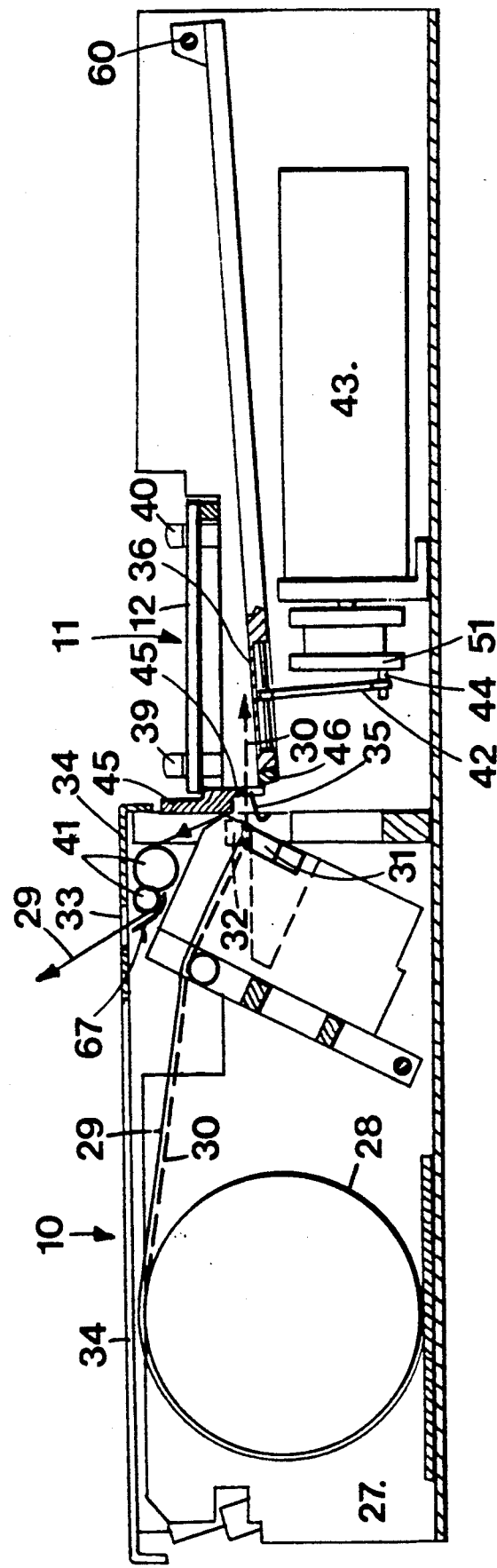
FIG. 4 is a longitudinal section according to 4—4 of FIG. 3, which shows the facility for printing, advancing and cutting the paper.

The structure and operation of the printing unit 10 and the associated receiving facility 11 forming part of the programming device 1 will now be described. In FIG. 2, it is seen that the programming device 1 takes the form of an attaché-case, whose lid 26 is detachable. In FIGS. 3 and 4, the facility for printing on a self-adhesive paper tape is seen with, in addition, the means providing for the separation of the printed paper tape from the tape acting as backing for it, as well as the cutting to format of the printed tape thus separated from its backing and the sticking of the cut portion of tape onto the data medium 12. All these components are arranged in a frame 27. The roll of paper feeding the printing facility is seen at 28. The backing tape is shown as a continuous line at 29, and the paper tape designed to receive the printing is shown as a broken line 30. The reason for the presence of the backing 29 is that the tape 30 is self-adhesive. The assembly of tapes 29 and 30 coming from the roll 28 enters the printer, where they pass together between the printing head 31 and an anvil 32, after which the tapes 29 and 30 are separated, as will be seen later, and the backing tape 29 emerges through a slit 33 in a lid 34 of the printing mechanism. The printed tape 30 arrives in contact with a fixed guide 35, which forces it to pass between the two open blades of a scissors, as will be seen below, and to arrive above a swinging table 36 arranged below the receiving facility 11. A data medium 12 is seen to be arranged in this receiver 11.

In FIG. 3, the data medium 12, in the form of a credit card, is seen with its connector 37, and the connector of the receiving facility 11 is seen at 38. A data medium 12 is shown as a chain-dotted line at 12a, at the place which it occupies in the receiving facility 11. The medium 12 is held in place in the receiving facility 11, on the one hand by the interaction of the connectors 37, 38, and by the action of two retaining springs 39, 40. To provide for the cutting of a section of tape 30 to the dimension of the medium 12, the microprocessor 6 controls a facility 41 for driving the tape 29. The separation between the tapes 29 and 30 takes place automatically as a result of the small angle between the point of arrival and the point of departure of the tape 29 driven by 41. The tape 30, for its part, continues horizontally, being controlled by 35. When the tape 30 has advanced by the required amount, that is to say by the dimension of the medium 12, the table 36, controlled by the connecting rod 42, actuated by a motor 43 via a crank 44, swings upwards. This tape 30 passes through the gap between a fixed blade 45 of a pair of scissors, the other blade 46 of which is carried by the table 36. The raising of the table 36 produces the cutting of the paper. The upper surface of the cut tape section is that which is self-adhesive, and the raising movement of the table 36 is continued until the cut section becomes applied against the lower face of the medium 12. The continuation of the rising movement of the table 36 causes the extraction of the medium 12 from the receiving facility 11, this medium being detached from the connector 38 and the springs 39, 40 being pushed back.

The length of the table 36 corresponds to the length of the sections of tape 30 on which, as seen above, the complete detailed program recorded, moreover, on the data medium 12 is printed. There may, moreover, be several tape sections for containing, in a form written in interactive language, the whole of a program.

It is necessary to ensure that the section of tape 30, which advances along the table 36 and which is adhesive-coated on its upper face, remains properly in position on this table and does not run the risk of distorting and sticking somewhere, producing jamming. To this end, the following means are provided. Over the length of the table 36 which corresponds to the length of a section of tape 30 that is required to stick to the data medium 12, two rows of rollers 47, 48 are provided, each row carried by a rectilinear part 49 and 50, respectively, parallel to the longitudinal general direction of the table 36. The bars 49 and 50 are movable, as will be explained in connection with FIG. 8, so that they can be separated from one another by a certain amount. In the normal position, the rollers 47, 48 are above the longitudinal edges of the table 36, at a very short distance from the latter, the distance being just sufficient to allow the portion of tape 30 to pass between these rollers and this table. In other words, these rollers 47, 48 keep the tape flat on the table 36.

Figure 8:
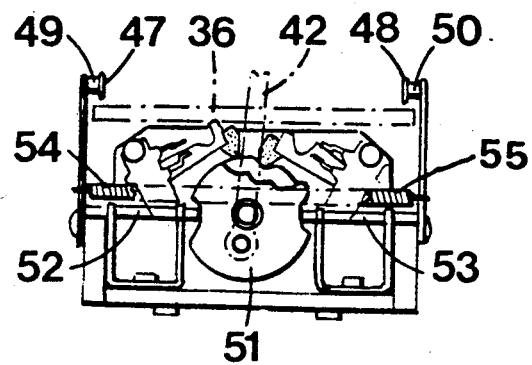
FIG. 8 is a detail view from the left in FIG. 4.

In FIG. 8, the bars 49, 50 are shown in normal position of maximum proximity. In FIG. 3, on the other hand, these bars are shown in the separated position where the rollers 47, 48 are beyond the longitudinal edges of the section of tape 30. This is arranged in order to leave room for the table 36 in its upward movement, which provides for the cutting of the paper, the application of the cut section of tape 30 and the ejection of the data medium 12.

It has been described above how the movement of the table 36 is produced. The movement of separation of the bars 49, 50 is, for its part, also produced by the motor 43, via a cam 51 driven by the motor 43, this cam acting on two coaxial sliding rods, 52, 53 pulled by return springs 54 and 55, respectively. The rotation of the cam forces the rods 52, 53 to move apart from one another, thereby causing the separation of bars 49, 50. The return springs 54, 55 automatically bring these bars back to the normal position. It is obvious that the cam 51 and the connecting rod. 42 act in synchrony, being driven by the same motor, thereby ensuring that the bars 49, 50 and the rollers which they support separate immediately before the table 36 starts to rise, and that these bars come back to the normal position only after the table 36 has returned to the lower position.

The part of the table 36 situated beyond the receiving facility 11 is equipped with two bars attached to it, 56, 57, which are in the exact line of projection of the bars 49, 50 when the latter are in the normal position. These bars 56, 57 are each equipped with a series of rollers, 58, 59, similar to the rollers 47, 48 and fulfilling the same function of keeping the paper tape applied on the table 36 up to the point at which the free end of this tape reaches the end of the table. In the interest of simplification, the bars 49, 50, 56 and 57, and likewise the rollers which they carry, have not been shown in FIG. 4.

Figure 9:
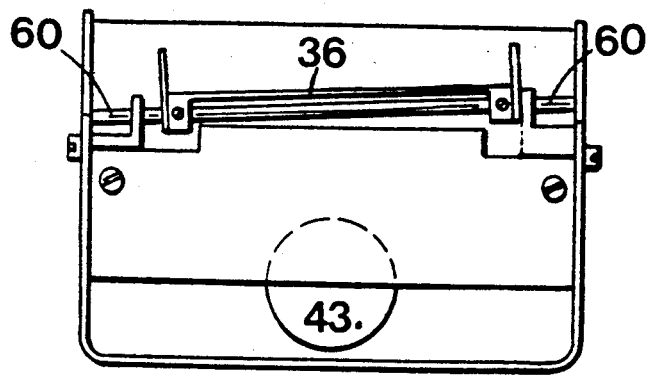
FIG. 9 is a side view from the right of FIG. 4.
Figure 10:
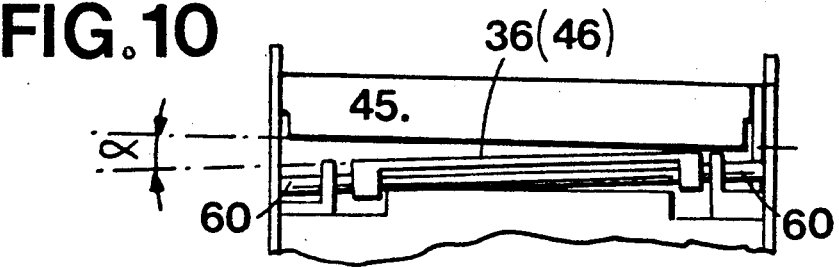
FIG. 10 is a detail view from the right of FIG. 4, showing the paper cutting mechanism.

As regards the cutting of the paper tape, as shown in FIGS. 9 and 10, a fixed tilting of the table 36 is arranged in the transverse direction. In FIGS. 9 and 10, the slightly oblique fixed axis about which the table 36 swings under the control of the connecting rod 42 is seen at 60. The angle formed by this axis, and consequently the table 36, with respect to the horizontal, which coincides here with the cutting edge of the knife 45, is seen at $a$. The upward swinging movement of the table 36 causes the blades 45 and 46 to act in the manner of a pair of scissors.

As regards the actual printing mechanism, this is of a known type, and the description will be limited to that which follows, reference being made to FIGS. 5, 6 and 7. The printing head 31 is a thermal printing head mounted slideably on a transverse fixed rod 61 so as to move along this rod under the control of a screw 62 whose axis is parallel to that of the rod 61. The backward and forward movement of the printing head 31 is controlled by a stepping motor 63, via a gear train 64. The printing head 31 is applied by a spring, not shown, against the anvil 32 (FIGS. 4 and 6), or more exactly against the assembly of tapes 29 and 30 passing between this head and this anvil.

The driving of the paper (29, 30) is produced by a stepping motor 65, via a geared reduction 66 which drives the rollers 41. The paper which leaves the second of the rollers 41 (which does not drive) to pass through the opening 33 is guided by a fixed guide 67. FIG. 5 shows the members of the printing mechanism in the working position, while FIG. 7 shows these same members in the position in which the paper is placed between the two rollers 41, that is to say in the position in which these two rollers are separated from one another. The change from one of these positions to the other is carried out by grasping a transverse rod 68 which is firmly attached at both ends to a pair of locking parts 69. These parts 69 are articulated at 70 on a lever 71 swinging about a fixed axis 72. A pair of levers 73, carrying at their upper end the paper clamping roller belonging to the group 41, can swing about the axis 70. The driving roller of the group 41 rotates in two lateral flanges 74 of the facility which, in the interest of simplification, have not been shown in FIGS. 5 and 7. It is seen that, by grasping the rod 68 so as to cause it to swing in the direction of the arrow 75, the following effects are caused. Each of the parts 69, which has a rectilinear slot 76 equipped at its ends with two notches 77, 78, moves from the position according to FIG. 5 towards that according to FIG. 7. In FIG. 5, the notch 77 interacts with two transverse coaxial rods 79, whereas in the position according to FIG. 7, these rods 79 interact with the notch 78. In addition, the lever 71, as a result of its articulation 70 on the part 69, is driven by the latter to rotate about 72 and reach the position according to FIG. 7. Simultaneously, the lever 73, also as a result of its articulation at 70, is driven by the part 69 and comes to the position shown in FIG. 7. A fixed stop 80, however, stops the lever 73 during its travel, the effect of which is to separate the clamping roller of the group 41 from the driving roller of this group, as seen in FIG. 7. This stopping and this separation of the two rollers 41 are made possible by a double spring 81 mounted around 70 and acting by its two ends on 68 and on an axis 82 of the lever 73, respectively, tending to separate these two axes from one another. The spring 81 has two effects: on the one hand, it tends to apply the free roller of the group 41 against the driving roller, and on the other hand, it tends to apply the notch 77 against 79. This spring 81, by yielding during the movement from the position according to FIG. 5 to that according to FIG. 7, enables the lever 73 to stopped by 80 in the course of motion, and consequently makes it possible to provide for the separation of the roller.

The installation described possesses a number of advantages, which may be summarized in the following manner. In the first place, the automatic sticking of the patient's identification data onto the data medium itself while it is still in the programming device fully combats all possibility of error in identifying the medium. The manner in which the programming device and the stimulating device are constructed for on-line working enables, as a result of the use of data media of the smart card type, the data media to be stored while releasing the stimulating device after use by each patient, the need to re-record a program already used being eliminated. In addition, the use of RAMs in the data medium permits modification and addition at will to the program which is recorded on the data medium, thereby remedying the defect of ROM systems. Finally, the possibility is offered by the installation, as described above, of enabling the therapist to check whether the patient has indeed complied with the treatment laid down, and to detect, where appropriate, whether he has cheated.

What is claimed is:

1. Installation for neuromuscular electrical stimulation comprising, a programming device containing an alphanumeric control keyboard, a display screen, a microprocessor and a program memory, and at least one electrical stimulating device arranged for on-line working with the programming device, at least during a programming phase, and for working independently during the treatment of a patient, wherein the programming device (1) contains a facility (11) for receiving a removable and interchangeable programmable data medium (12), said facility being equipped with a connector (38) arranged to interact with a corresponding connector (37) possessed by said data medium (12) when it is placed in said facility (11), said medium being designed to receive a patient's treatment program, completely and in an individual manner, and to control the stimulating device (2) during treatment of the patient, wherein the stimulating device (2) contains a facility (25) for receiving one said data medium (12) which has been programmed beforehand on the programming device (1), according to a first, general version of an individualized program designed for a particular patient, said receiving facility (25) and said medium each being equipped with an electrical connector arranged to interact one with the other, and wherein an on-line link (3), when it is established, is arranged so as to provide for the electrical linkage between the keyboard (8) of the programming device (1) and the said receiving facility (25) of the stimulating device (2) in order to provide for the modification, by using the keyboard (8) of the programming device (1), of the first version of the program on the data medium (12) placed in the receiving facility (25) of the stimulating device (2), this being done by an operator in accordance with the patient's individual features and his reactions during a test of stimulation by means of the stimulating device (2), in order that a program thus modified shall be completely individualized and adapted to the patient's case, means (6, 17) being provided for modifying, simultaneously and in the same manner, the program in the program memory (7) of the programming device (1), the data medium (12) being from this point capable of controlling the stimulating device (2) operating independently, for the treatment of the patient corresponding to this data medium (12) temporarily in position in the receiving facility (25) of the stimulating device (2); and also having means (11, 6, 8) for transferring into the memory (7) of the programming device (1) a standard program recorded beforehand on a first said removable and interchangeable data medium (12) and suitable as a first approximation for a given patient, when said first medium (12) is placed in the receiving facility (11) of said programming device (1), means (8, 6, 11) being provided for transferring onto a second said removable and interchangeable data medium (12) then placed in said receiving facility (11) as a replacement for the first medium, the standard program thus recorded in the memory (7) of the programming device (1), after which this program, as a first approximation, thus recorded on the second data medium (12) is modifiable, by the use of the keyboard (8), simultaneously on this data medium

(12) and in the program memory (7) in order to individualize it at least partially to the case of a given patient; wherein the programming device (1) and stimulating device (2) are constructed so as to provide for an additional modification, simulataneously on the medium (12) and in the memory (7) of the programming device, of the program already modified in the programming device (1), when the data medium (12) is placed in the receiving facility (25) of the stimulating device (2) and when the on-line link (3) is established between the two devices (1, 2), in order to refine the program and individualize it completely in accordance with the patient's reactions during the test of stimulation by means of the stimulating device (2).

2. The installation as claimed in claim 1, wherein the stimulating device (2) contains means (17, 18, 25) for recording on the data medium (12) placed in the receiving facility (25) of the stimulating device (2), during the treatment when this device (2) is operating independently, the period during which this stimulating device (2) operates and the period during which, for each of its outputs (21, 22, 23, 24) with electrodes (21a, 22a, 23a, 24a) for application to the patient contained by this device, the intensity of the working current is between minimum and maximum limits programmed and recorded on this data medium (12).

3. The installation as claimed in claim 1, wherein the programming device (1) contains a printing facility (10), for printing on a portion of a self-adhesive tape (30) at least the patient's identification data, when the individualized programming is finished and recorded on the data medium (12), while this medium is placed in the receiving facility (11) of the programming device (1), and wherein it contains a facility (45, 46, 36) for cutting, applying and sticking automatically the said portion of printed self-adhesive tape onto the data medium (12) present in this receiving facility (11), and for then ejecting this medium thus equipped with this printed portion identifying the patient to which this medium corresponds.

4. The installation as claimed in claim 3, wherein the programming device (1) contains means (6, 7) for actuating the printing facility (10), in order to cause it to print, uncoded and completely, on at least one other portion of self-adhesive tape (30), under the control of the memory (7), the individualized program as recorded in this memory (7) and, in addition, the patient's identification data.

5. The installation as claimed in claim 3, wherein the printing facility (10) of the programming device (1) contains mechanical means (41, 32) for separating the printed portion of the self-adhesive tape (30) from its backing (29), and for cutting it to the format of the data medium (12) and to another format for applying and sticking the portion cut to the format of the medium (12) onto this medium, before the means for ejection of this medium produce this ejection.

6. The installation as claimed in claim 1, wherein the data medium (12) is of the smart card type and assumes at least approximately the format of an ordinary credit card.

* * * * *